(12) United States Patent
Heinonen et al.

(10) Patent No.: US 10,835,177 B2
(45) Date of Patent: Nov. 17, 2020

(54) ANESTHESIA ASSESSMENT SYSTEM AND METHOD FOR LUNG PROTECTIVE VENTILATION

(71) Applicant: General Electric Company, Schenectady, NY (US)

(72) Inventors: Erkki Heinonen, Helsinki (FI); Tali Gordon Ben-Ami, Madison, WI (US); Tom J. Häggblom, Helsinki (FI)

(73) Assignee: General Electric Company, Schenectady, NY (US)

( * ) Notice: Subject to any disclaimer, the term of this patent is extended or adjusted under 35 U.S.C. 154(b) by 742 days.

(21) Appl. No.: 15/612,109

(22) Filed: Jun. 2, 2017

(65) Prior Publication Data
US 2018/0344958 A1 Dec. 6, 2018

(51) Int. Cl.
*A61B 5/00* (2006.01)
*A61M 16/14* (2006.01)
(Continued)

(52) U.S. Cl.
CPC ............ *A61B 5/486* (2013.01); *A61B 5/4836* (2013.01); *A61M 16/01* (2013.01); *A61M 16/0463* (2013.01); *A61M 16/12* (2013.01); *A61M 16/14* (2013.01); *A61B 5/021* (2013.01); *A61B 5/02055* (2013.01); *A61B 5/02405* (2013.01);
(Continued)

(58) Field of Classification Search
CPC .. A61M 16/01; A61M 16/12; A61M 16/0463; A61M 16/0051; A61M 16/0069; A61B 5/02055; A61B 5/4836; A61B 5/486
See application file for complete search history.

(56) References Cited

U.S. PATENT DOCUMENTS

| 8,695,594 B2 | 4/2014 | Tham et al. |
| 2009/0241957 A1 | 10/2009 | Baker, Jr. |
| 2010/0275920 A1 | 11/2010 | Tham et al. |

FOREIGN PATENT DOCUMENTS

| CN | 105413030 A | 3/2016 |
| WO | 2008/148134 A1 | 12/2008 |
| WO | 2016/096391 A1 | 6/2016 |

OTHER PUBLICATIONS

International Search Report and Written Opinion issued in connection with corresponding PCT Application No. PCT/US2018/033414 dated Sep. 3, 2018, 10 pages.
(Continued)

*Primary Examiner* — Max F Hindenburg
(74) *Attorney, Agent, or Firm* — Andrus Intellectual Property Law, LLP (57) ABSTRACT

A method and system for assisting clinicians in determining when and how to perform a lung recruitment procedure. The method includes a user configurable interface that an operator or institution can set up to correspond to best practices. Based upon the information entered into the configurable user interface, a method and algorithm automatically determines when a lung recruitment procedure should be instituted. The system can either manually or automatically enable the beginning of the lung recruitment procedure depending upon the clinician and facility preferences. The algorithm includes a plurality of process steps that are carried out in a clinically-relevant order to eliminate patient condition options and to provide the appropriate recommended actions prior to initiating the lung recruitment procedure.

20 Claims, 9 Drawing Sheets

(51) Int. Cl.
  *A61M 16/04* (2006.01)
  *A61M 16/12* (2006.01)
  *A61M 16/01* (2006.01)
  *A61B 5/0205* (2006.01)
  *A61B 5/021* (2006.01)
  *A61B 5/024* (2006.01)
  *A61B 5/083* (2006.01)
  *A61B 5/085* (2006.01)
  *A61B 5/145* (2006.01)
  *A61M 16/10* (2006.01)
  *A61M 11/00* (2006.01)

(52) U.S. Cl.
  CPC ............ *A61B 5/085* (2013.01); *A61B 5/0833* (2013.01); *A61B 5/0836* (2013.01); *A61B 5/14542* (2013.01); *A61B 5/7275* (2013.01); *A61B 2505/03* (2013.01); *A61B 2505/05* (2013.01); *A61M 11/00* (2013.01); *A61M 2016/1025* (2013.01); *A61M 2202/025* (2013.01); *A61M 2202/0208* (2013.01); *A61M 2202/0266* (2013.01); *A61M 2202/0283* (2013.01); *A61M 2205/505* (2013.01); *A61M 2230/205* (2013.01); *A61M 2230/30* (2013.01); *A61M 2230/432* (2013.01); *A61M 2230/435* (2013.01); *A61M 2230/46* (2013.01); *A61M 2230/50* (2013.01)

(56) References Cited

OTHER PUBLICATIONS

Unpublished U.S. Appl. No. 15/402,809, filed Jan. 10, 2017.

| Adequate ventilation assessment | 13:20 | 12:50 |
|---|---|---|
| EtCO2 (mm Hg) | 50% | 45% |
| Δ Insp-Exp O2 | 5% | 5% |

| Atelectasis assessment | 13:20 | 12:50 |
|---|---|---|
| Working Pressure | 22 cmH2O | 15 |
| Cstat | 30 | 40 |

Start Lung Recruitment Procedure.

| Start | Check again in 5 minutes | Cancel |
|---|---|---|
| 114 | 116 | 118 |

| Lung Assessment Dashboard | 13:20 | 12:50 |
|---|---|---|
| SpO2 (%) | 90% | 95% |
| EtO2 (%) | 30% | 50% |
| EtCO2 (mmHg) | 50% | 45% |
| Δ Insp-Exp O2 | 5% | 6% |
| MAP (mmHg) | 65 mmHg | 58% |
| PPV (%) | 20% | 18% |
| Δ RAW from last measurement | | |
| Working Pressure | | |
| Cst at | | 15% |

ANESTHESIA ASSESSMENT SYSTEM AND METHOD FOR LUNG PROTECTIVE VENTILATION

BACKGROUND

The present disclosure is related to the field of respiratory therapy and anesthesia delivery. More specifically, the present disclosure is related to a system and method of standardizing lung recruitment maneuvers for clinicians and facilities.

Mechanical ventilation is a commonly accepted medical practice in the treatment of individuals experiencing respiratory problems. During surgery, patients are paralyzed and lose control over their airway, completely or partially, thus requiring mandatory or support ventilation. In these instances, mechanical ventilatory assistance is provided by the anesthesia system's ventilator or an ICU ventilator.

Generally, lung function can be improved by recruitment, wherein the increases in lung volume translate into increased surface area for gas exchange, versus derecruitment, wherein lung volume and surface area for gas exchange is reduced. Derecruitment in the lungs can be a sign of more severe physiological conditions. If derecruitment is detected, the condition can sometimes be reversed using a variety of techniques directed to promoting recruitment of lung volume to recover the lost capacity for effective gas exchange.

Currently, lung recruitment is often a manual maneuver, performed by manually squeezing the ventilation bag. How and when it is done is varied from clinician to clinician and care facility to care facility. Such a situation makes it difficult to optimize the patient's conditions under which a recruitment procedure (also know in published literature as a lung recruitment maneuver) is applied and standardize the maneuver's recommended settings within a care facility.

Additionally, there is a missed opportunity to gather analytics and provide feedback to clinicians to optimize within facility procedures. Lastly, there is a missed opportunity to provide data based automatic recruitment or recommendations on recruitment based on measured data.

SUMMARY

The present disclosure generally relates to a method and system for determining when a lung recruitment procedure may be desired for a patient receiving respiratory support from an anesthesia system or an ICU mechanical ventilator. The method and system of the present disclosure standardizes the determination of when a lung recruitment procedure should be applied to a patient to increase consistency within a healthcare facility.

The method obtains a plurality of patient parameters from the patient during the respiratory support. Prior to beginning the decision process, a plurality of default parameters are set by an operator or healthcare facility and the default parameters are stored in a processor. The default parameters may relate to the normal operating range for the parameters obtained from the patient or may relate to the preferred type of lung recruitment procedure to be carried out by the ventilator. The operator is presented with visual indicators and data entry points such that the operator can tailor the operation of the ventilator for the individual patient or based on the preferences of the operator. However, the default parameters allow a facility to create a preferred protocol of action for all patients receiving respiratory support that must be adjusted by the operator.

After the default parameters have been set, the method compares the obtained patient parameters to the default parameters that are stored in the processor. Based upon this comparison, the method carries out a series of processing steps to make various sequential assessments about the patient's condition prior to suggesting the beginning of a lung recruitment procedure. The various processing steps and assessments utilize different patient parameters and are sequentially carried out by the method of the present disclosure.

If all of the sequential assessment steps are carried out and confirmed by the operator, a processor of the ventilator will suggest beginning a lung recruitment procedure. In an alternate embodiment, the processor may begin the lung recruitment procedure automatically without the need for confirmation by an operator.

The method of the present disclosure allows an operator to select between a plurality of different lung recruitment procedure types. These lung recruitment procedure types each dictate the way the lung recruitment procedure is carried out by the ventilator. In addition to selecting between the plurality of different lung recruitment procedure types, the method allows the operator to adjust default parameters for the selected lung recruitment procedure type to further tailor operation of the ventilator.

In accordance with one aspect of the present disclosure, a series of sequential process and assessment steps are carried out prior to a recommendation for the beginning of a lung recruitment procedure. These sequential process steps can include an oxygen supply assessment, an adequate ventilation assessment, an adequate profusion assessment and an atelectasis assessment. Once these assessments are completed, the method then suggests the beginning of a lung recruitment procedure. The lung recruitment procedure can be started by the operator, delayed or ignored by the operator. Alternatively, the ventilator can automatically initiate the lung recruitment procedure upon all of the assessment steps being completed and the patient parameters indicating the need for the lung recruitment.

DETAILED DESCRIPTION

Figure 1:
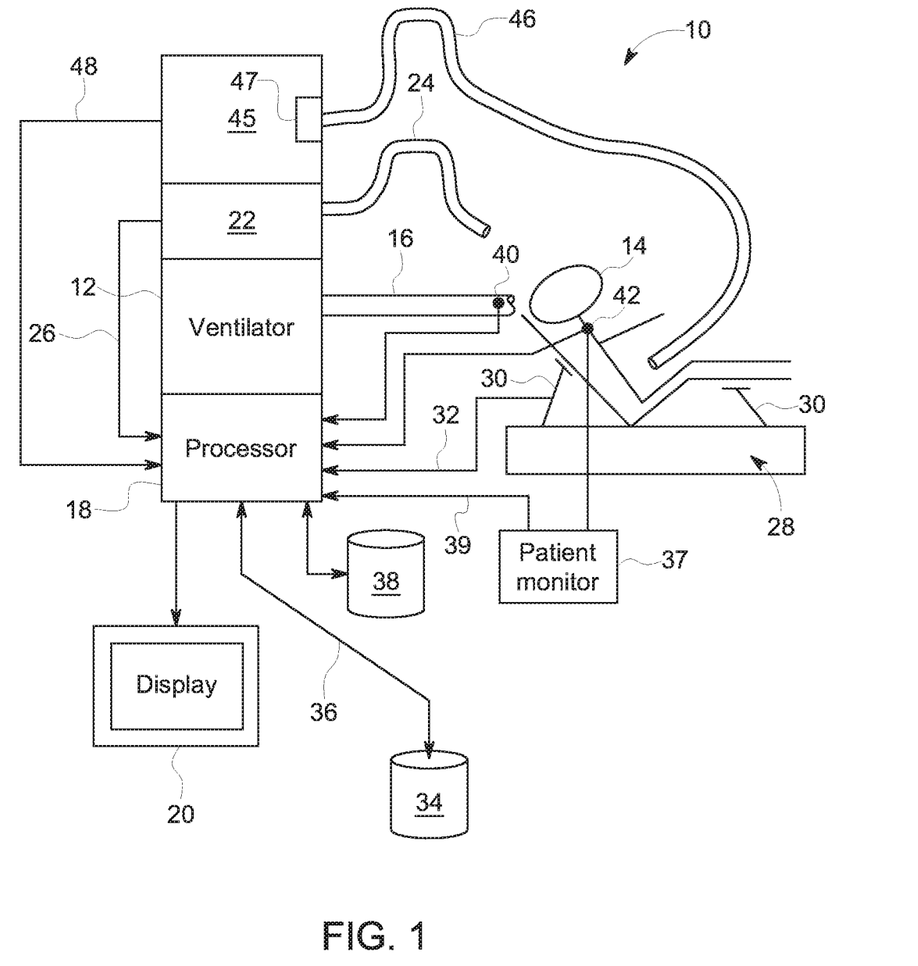
FIG. 1 is a schematic diagram of an exemplary respiratory support system.

FIG. 1 is a schematic diagram of an exemplary embodiment of a respiratory support system 10. The system 10 includes a mechanical ventilator 12. The mechanical ventilator 12 provides medical gas to a patient 14 through a breathing circuit 16. The medical gas supplied to the patient 14 by the ventilator 12 may be any of a variety of known medical gases that include, but are not limited to, one or more of oxygen, nitrogen, nitrous oxide, helium, heliox or others. Additionally, the mechanical ventilator 12 may also deliver vaporized medication to the patient such as anesthetic agent or other drugs.

A processor 18 is communicatively connected to the mechanical ventilator. In one embodiment, the processor 18 is an integral part with the mechanical ventilator 12 and in an alternative embodiment, the processor 18 is part of a stand-alone device that may be, but is not limited to, a personal computer or hand-held device. In an embodiment wherein the processor 18 is part of a separate or mobile device, this embodiment may be particularly useful for monitoring a patient during periods of transition between rooms and medical equipment. The processor 18 is, in any embodiment, communicatively connected to the mechanical ventilator 12, such that the processor 18 is able to receive information from the mechanical ventilator 12 as described in further detail herein and is able to control or operate or at least modify the control or operation of the mechanical ventilator 12, such as disclosed in further detail herein.

The processor 18 is communicatively connected to a graphical display 20. The graphical display 20 is configured to visually present information to a clinician as disclosed in further detail herein. As with the processor 18, the graphical display 20 may be an integral part of a single unit that includes the processor 18 and mechanical ventilator 12. In an alternative embodiment, the graphical display 20 is part of a stand alone device that is either integrated with, or communicatively connected to, the processor 18.

The processor 18 is further at least communicatively connected to a variety of peripheral systems. These peripheral systems include components of the mechanical ventilator 12 and/or otherwise separate devices that are used in the monitoring and treatment of the patient 14. One example of a peripheral system is a suction machine 22. The suction machine 22 is connected to a suction catheter 24 that is used to perform a suction procedure on the patient's lungs and/or airway. A suction machine 22 is one therapeutic tool available to a clinician in order to remove a buildup of fluid, mucous, or other substances within the lung and/or airway of the patient 14. The suction machine 22 is communicatively connected to the processor 18. The suction machine 22 provides a suction signal 26 to the processor 18 to indicate that a suction procedure has been performed.

An alternative peripheral system is that of bed 28. The bed 28 is an electro-mechanical bed that may be adjusted to provide comfort and/or therapeutic support to the patient 14. Such adjustments to the position or angle of the bed may be to elevate the feet of the patient 14, or to incline the patient's torso to a generally seated position. The bed 28 may be a surgical bed that can be articulated and inclined to facilitate laprascopic or abdominal robotic surgeries. One such articulation includes tilting the bed 28 in a Trendelenburg position where the feet of the inclined patient 14 are elevated above the head. Bed sensors 30 detect the position and/or angle of the configuration of components of the bed 28 and provide a bed signal 32 from the bed sensors 30 to the processor 18 indicative of the detected position and/or angle.

Another peripheral system is that of a gas insufflation machine 45. The gas insufflation machine adds gases (such as carbon dioxide) into the abdomen of patient 14 through the tube 46. The gas insufflation machine 45 further regulates the gas pressure introduced into the patient's abdomen that distends the abdomen for laprascopic or robotic surgeries to be conducted within the closed abdominal cavity. Insufflation sensors 47 detect the gas delivery and distending pressure of the abdomen of the patient 14 and provide an insufflation signal 48 to the processor 18 indicative of the detected abdominal insufflation.

In a still further embodiment, the processor 18 is communicatively connected to an electronic medical record (EMR) 34 of the patient 14. The EMR 34 may be stored at a location remote from the processor 18, such as a centralized hospital information system or server. The processor 18 may be communicatively connected to the EMR 34 through a hospital intranet, or the Internet using a wired or wireless data communication platform. The EMR 34 can be a peripheral system itself or can serve as an aggregator of information from a variety of peripheral systems used with the patient. These peripheral systems may be imaging systems, surgery systems, food service systems, or other monitoring or treatment systems in the clinical setting as would be recognized as applicable to the presently disclosed systems and methods by one of ordinary skill in the art. Exemplarily, imaging information such as CT scans or PET scans can perform imaging of the lungs that can indicate derecruitment, the detection of such an event, indicated in the EMR can be provided to the processor 18. The EMR 34 may be updated by a clinician or clinicians that perform various tasks or procedures on the patient 14 and record the information in the EMR 34. Therefore, the processor 18 is able to obtain an EMR signal 36 that is indicative of events involving one or more of a variety of other peripheral systems that are not immediately located with the patient 14 and the mechanical ventilator 12.

Finally, the mechanical ventilator 12 itself may include a variety of peripheral systems as used in the present disclosure. The peripheral systems may be additional features of the mechanical ventilator 12 such as particular functions or modes of operation. The mechanical ventilator 12 provides a ventilator signal to the processor 18 that is indicative of the initiation or detection of these features or processes. Exemplary, but not limiting, features and processes in the mechanical ventilator may be indications of a switch between bag and vent modes on the mechanical ventilator 12, an indication of a delivery of 100% oxygen to the patient 14, an indication of a change in, or the elimination of, PEEP therapy provided by the mechanical ventilator 12 to the patient 14, or a detection that the breathing circuit 16 has been disconnected from the patient 14.

Thus, the peripheral systems as described above with respect to the respiratory support system 10 include a wide variety of devices, functions, or processes that may be performed in the monitoring and treatment of the patient 14. The signal provided by the peripheral systems to the processor 18 may be categorized as being indicative of particular events in the monitoring or treatment of the patient 14. As will be described in further detail below, events indicated by the peripheral systems may be related to or be indicative of an increased risk for lung derecruitment. The monitoring of these events by the processor 18 will be explained in further detail herein.

The processor 18 is connected to at least one, if not a plurality of physiological sensors. The physiological sensors may be connected directly to the processor 18 such that the sensor provides physiological sensors to the processor 18. Alternatively, the physiological sensors are components of a separate monitoring system, such as a patient monitor 37 that in turn provides the acquired physiological signals to the processor 18 along communication line 39. The patient monitor 37 is a conventional component that obtains a variety of physiological parameters from the patient through parameter modules and includes a display to present the obtained physiological parameters to a clinician.

The respiratory support system 10 is depicted with two exemplary physiological sensors. A gas analyzer 40 is disposed in the breathing circuit 16 in order to analyze the concentration of the component gases expired by the patient 14. Additional physiological parameters that may be obtained from the mechanical ventilator 12 or sensors associated therewith include a patient tidal volume and patient functional residual capacity (FRC). As exemplarily shown through these physiological parameter values from the mechanical ventilator, the physiological parameters may be parameters that are measured directly from the patient using the patient monitor 37, or may be derived parameters, such as FRC, that are calculated in known manners based upon a variety of measured values.

An alternative physiological sensor is that of biopotential sensor 42 that is affixed or otherwise attached to the patient 14. The biopotential sensor 42 may be any of a variety of biopotentials, including electrocardiogram (ECG), electromyogram (EMG), electroencephalogram (EEG), or electrical impedance tomography (EIT); however, these are not intended to be limiting on the types of biopotentials that may be monitored as physiological parameters in embodiments disclosed herein. Additionally, alternative sensors to the biopotential sensor 42 may measure physiological parameters from the patient 14, such as by the patient monitor 37. Exemplarily alternative sensors may include blood oxygen saturation (SPO2) or non-invasive blood pressure (NIBP), which are known physiological parameters in the field. Although only the single biopotential sensor 42 is shown in FIG. 1, it should be understood that the patient monitor 37 could be connected to a plurality of sensors attached to the patient. As will be described in further detail herein, physiological parameters measured by the physiological sensors may be related to, or indicative of an increased risk for lung derecruitment, particularly when analyzed in combination with other physiological parameters or derecruitment events.

The processor 18 is connected to a computer readable medium 38. The computer readable medium 38 may be an integral component with the processor 18 and the mechanical ventilator 12 in the form of computer memory. Alternatively, the computer readable medium 38 may be located remotely to the processor 18 and is only communicatively connected such as through the Internet or a hospital intranet. In these embodiments, the computer readable medium 38 may be a remotely located server.

Figure 2:
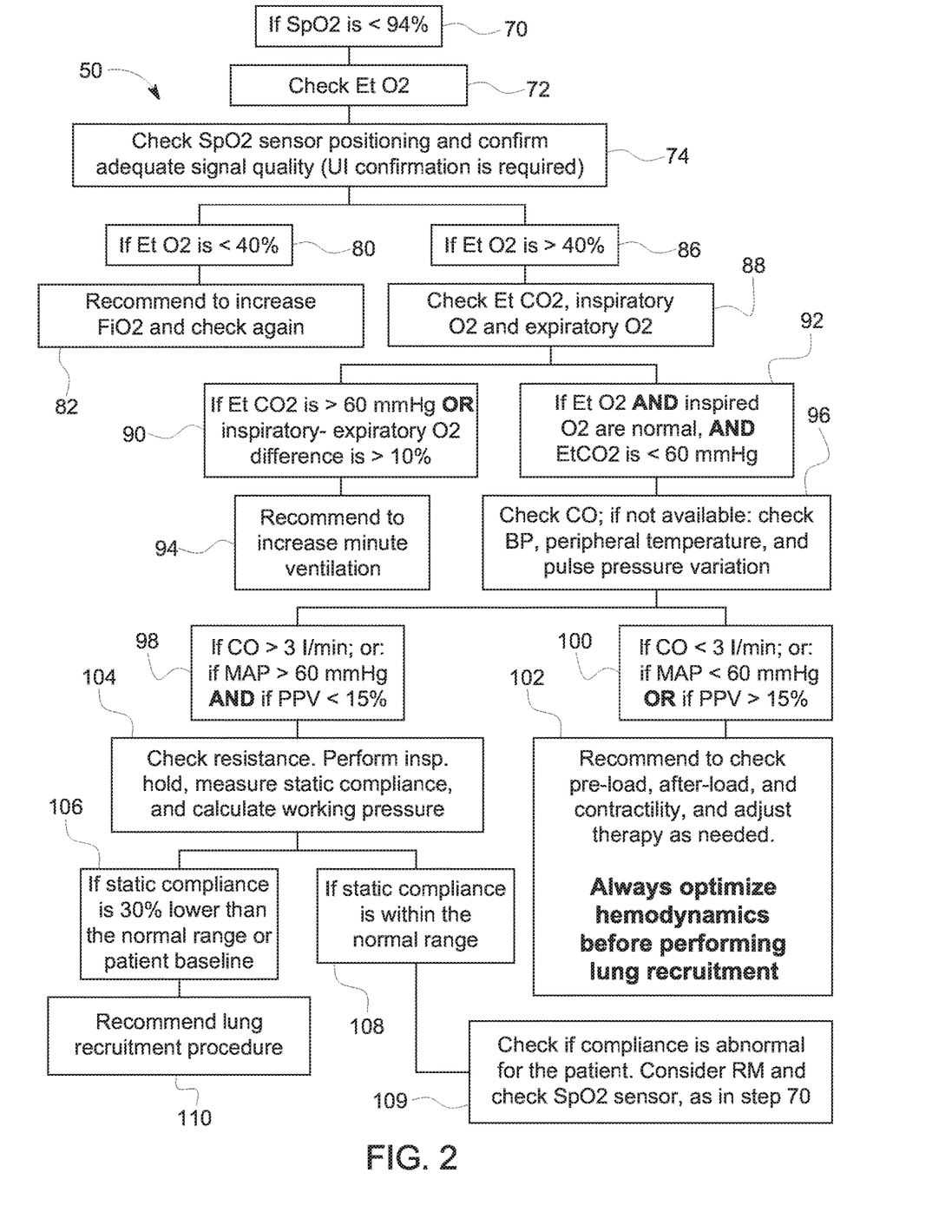
FIG. 2 is a flow chart depicting an embodiment of a method of determining whether a lung recruitment procedure should be initiated.

FIG. 2 is a flow chart depicting the steps of an embodiment of a method 50 for determining whether lung recruitment procedure therapy should be applied to a patient. The method 50 may be performed by the coordinated operation of the components of a system, such as the respiratory support system 10 of FIG. 1. Alternatively, the embodiment of the method 50 may be performed by a computer processor that is executing computer readable codes stored on a non-transient computer readable medium.

Figure 3:
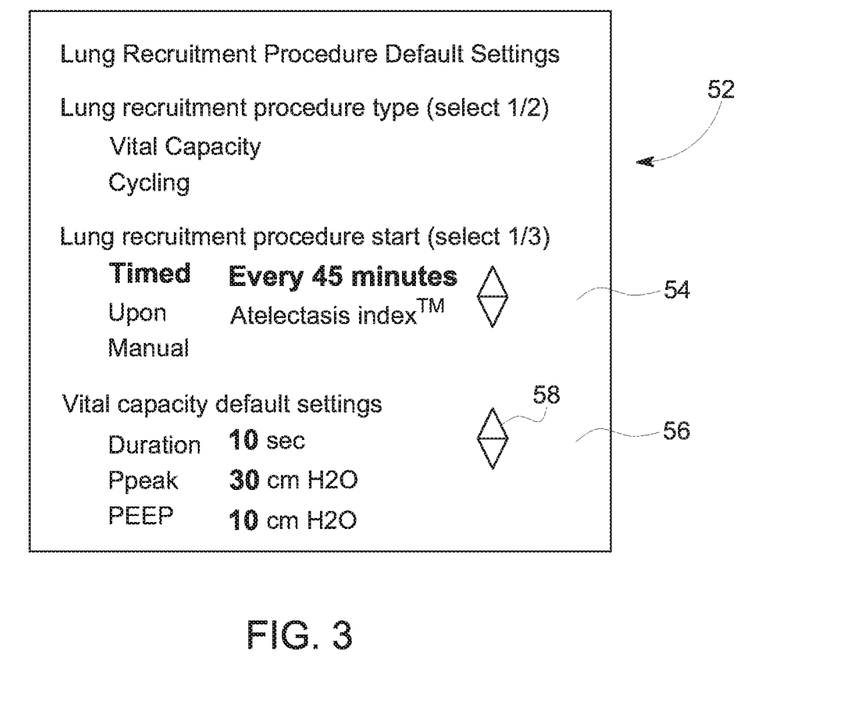
FIG. 3 is a display window providing on screen prompts for an operator to modify default settings of a lung recruitment procedure.

Prior to beginning the method 50 shown in FIG. 2, default settings for the lung recruitment procedure are entered into the processor of the ventilator for carrying out the lung recruitment procedure. FIG. 3 illustrates the initial default settings that are initially set by a facility and may be later adopted by an operator. These default parameters are pre-entered at the manufacturing site and can then be changed/modified by the healthcare facility utilizing the anesthesia system User Interface, a keyboard, mouse, touchscreen, touchpad or any other similar device that can be used to indicate a preference of the operator into the processor. In the parameter setting window shown by reference numeral 52, the operator is allowed to select between two different procedure types for performing lung recruitment. The two procedure types are referred to as vital capacity and cycling. The operator must select between the two procedure types and the operator is able to toggle between the two different recruitment procedure types.

Figure 4:
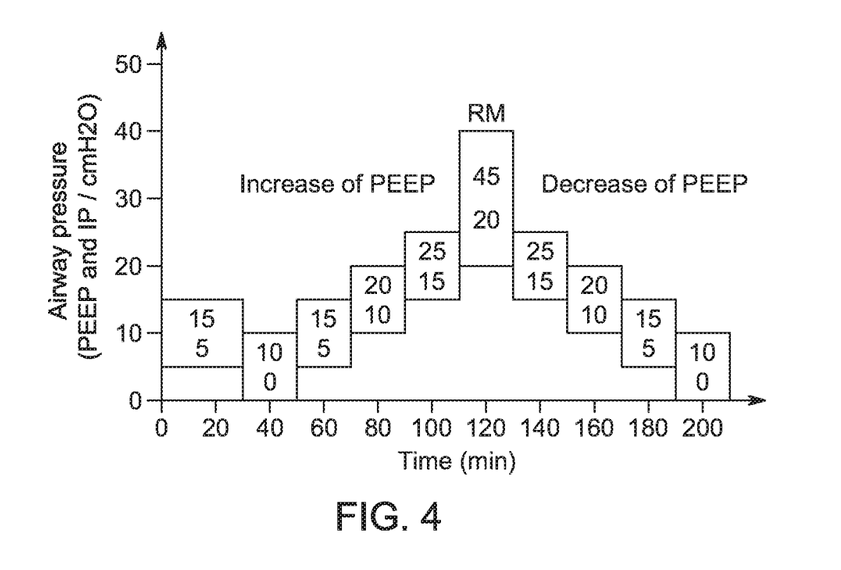
FIG. 4 is a graphic illustration of one of the lung recruitment procedures.

Once the operator selects the type of lung recruitment procedure to be carried out by the ventilator, the operator is next presented with a choice as to when the lung recruitment procedure should be started. The three options shown in FIG. 3 include starting the lung recruitment procedure based upon a time elapsed since the end of the last lung recruitment procedure, starting the procedure when the method 50 outputs a recommendation to start the lung recruitment procedure or upon a manual starting by the operator. The operator is required to select between one of the three options shown in area 54 of the window 52. The default timing is 45 minutes from the last procedure ending, which can be also adjusted by the operator. Prompt 56 allows the operator to adjust the default settings that relate to the lung recruitment procedure, an example profile of which is shown in FIG. 4. The operator can toggle between the various settings to control the duration of each procedure step, the pressure peak in each step as well as the PEEP value. As illustrated in FIG. 4, the lung recruitment procedure is graphically illustrated, which parameters can be adjusted by the operator.

The various different prompts shown in FIG. 3 are typically graphically presented to the user on a display along with one or more toggle buttons 58 that allows the user to adjust the various settings or selections. The use of the various prompts shown in FIG. 3 allows the operator to adjust the recruitment procedure default settings in a graphical manner. Prior to adjustment by the operator, the parameters are set at default values at the factory. The menu shown in FIG. 3 is used by the facility in which the ventilator is located to adjust factory default settings and preferences to match the system defaults with facility protocols. Since the default parameters can be adjusted and modified by the facility, the ventilator is operated utilizing the most preferred parameters for carrying out the lung recruitment procedure, unless modified by the operator.

Figure 5:
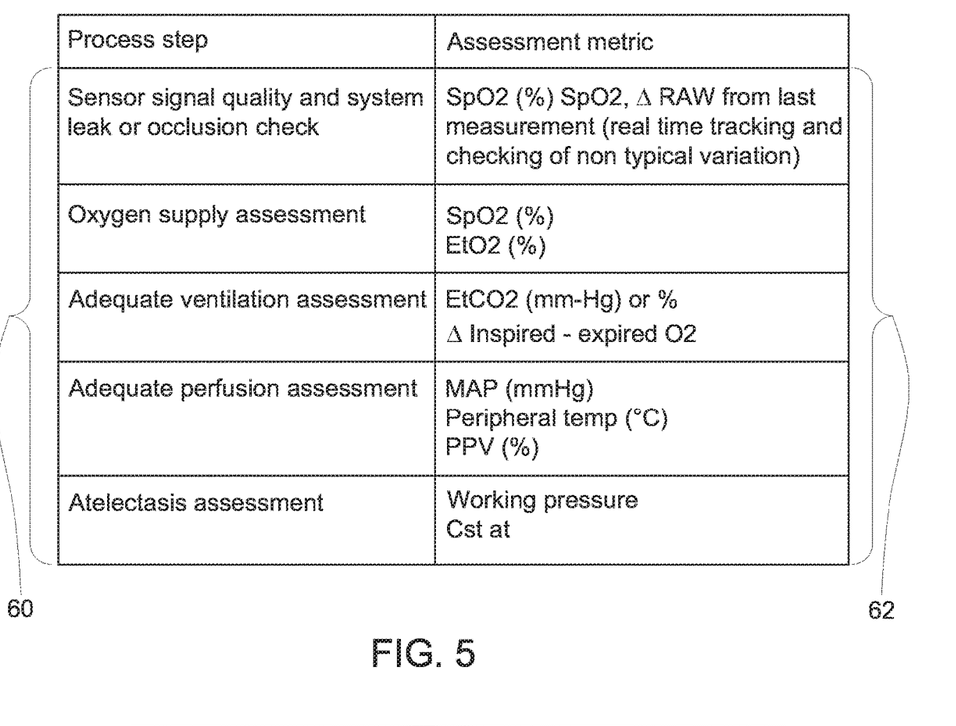
FIG. 5 is a table illustrating the different process steps performed in the flow chart of FIG. 2 and the metrics utilized for each of the process steps.

During the operation of the method 50 shown in FIG. 2, various different assessment steps are carried out in the method. The assessment steps are carried out before the method suggests initiation of the lung recruitment procedure to insure the recruitment procedure is delivered to the patient only when needed. FIG. 5 illustrates the various different assessments 60 that are made as part of the method steps of FIG. 2, as well as the metrics 62 used to make the various assessments. The different assessments 60 shown in FIG. 5 will be discussed in much greater detail with respect to the method 50 shown in FIG. 2.

Referring back to FIG. 2, the method initially begins in step 70. In step 70, the processor determines whether the SpO2 measured value from the patient is below a threshold value. In the embodiment shown in FIG. 2, the threshold value for the SpO2 measurement is 94%. However, this default value can be adjusted by the operator or facility.

If the method determines in step 70 that the SpO2 concentration has fallen below the threshold value (94%), the method proceeds to step 72 and begins an analysis step to check the end tidal oxygen concentration. These two steps correspond to the Oxygen Supply Assessment shown in FIG. 5.

Figure 6:
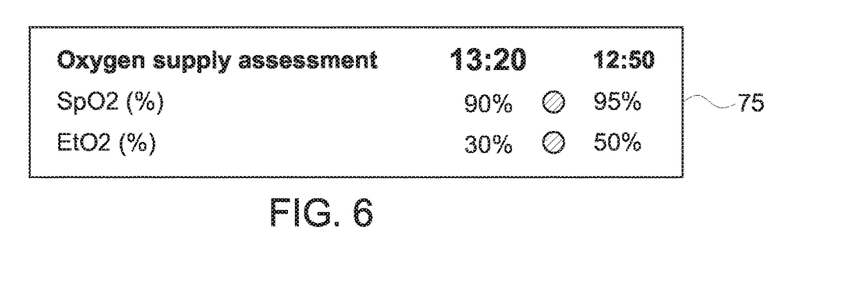
FIG. 6 is a display window showing the results of the oxygen supply assessment.

FIG. 6 is a display window 75 presented to the operator on the display to show the measured values from the patient for both the SpO2 and EtO2 at two different times in the monitoring of the patient. Separate indicators 73 can provide a visual indication through color as to whether the measured values for both the SpO2 and the EtO2 are within normal ranges. The indicators 73 are red when outside of the normal range and are green when inside the normal range. Other colors or additional colors could be used to provide additional information to the operator.

Figure 7:
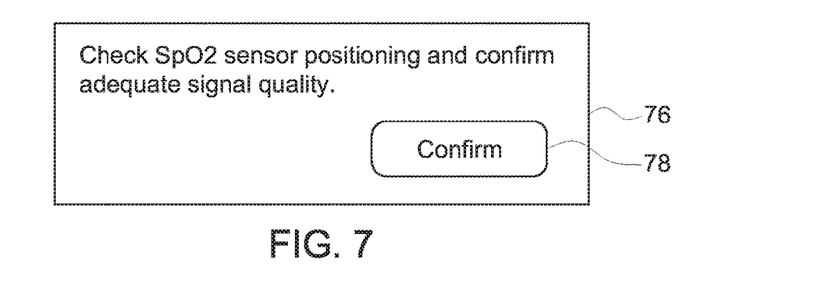
FIG. 7 is a popup window generated to the operator as part of the method of FIG. 2.

If the SpO2 and EtO2 values are outside of the normal ranges, as determined as part of this processing step, the method proceeds to step 74 and issues a popup window 76 to the operator, which is illustrated in FIG. 7. As shown in FIG. 7, the window 76 asks the operator to check the SpO2 sensor positioning and to confirm adequate signal quality from the SpO2 sensor. This is part of the Sensor Signal Quality and System Leak assessment shown in FIG. 5. If the SpO2 sensor is properly positioned, the operator confirms through the visual prompt 78.

Figure 8:
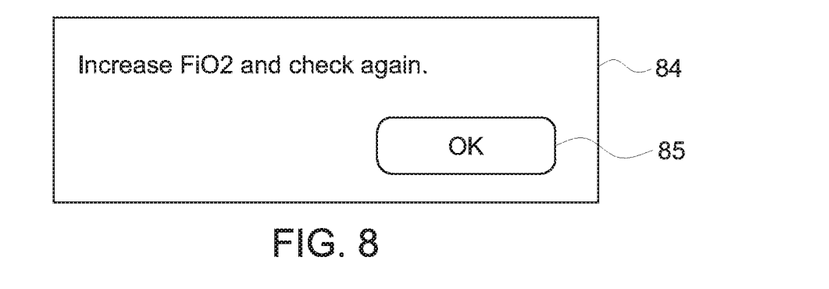
FIG. 8 is a popup window provided by a different portion of the method of FIG. 2.

Referring back to FIG. 2, once the sensor positioning and signal quality has been confirmed from step 74, the system acts based on the measured Et O2 concentration. The system compares the Et O2 concentration to a default threshold, which in the embodiment of FIG. 2 is set at 40%. If the Et O2 concentration is less than the default value (40%) as shown in step 80, the method proceeds to step 82 which requires additional action by the operator. In step 82, the method generates a popup window 84 which is shown in FIG. 8. The window 84 asks the operator to increase the FiO2 After the FiO2 has been increased and confirmed by button 85, the system waits for a predetermined amount of time, such as one minute, for the system to reach equilibrium. Once the system reaches equilibrium, the system again returns to step 72 to again check the Et O2 measurement.

Figure 9:
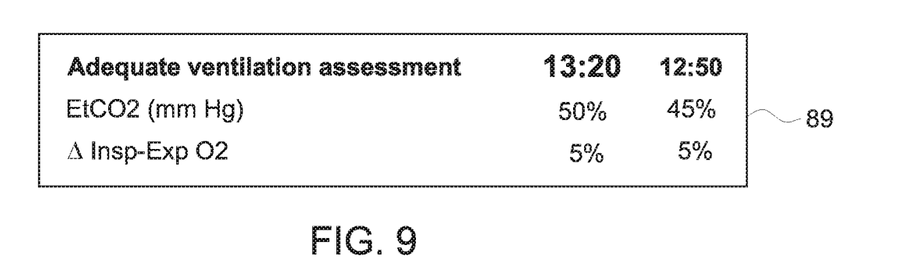
FIG. 9 is a display window showing the results of a ventilation assessment.

If the measured Et O2 is greater than the default value (40%), the method moves to step 86. Following step 86, the method proceeds to step 88 in which the Et CO2, inspiratory O2 and expiratory O2 measurements are made. These measurements are made as part of the Adequate Ventilation Assessment that is one of the process steps 60 shown in FIG. 5. After the measurements are made, the measurements are displayed to the operator in window 89, as shown in FIG. 9. FIG. 9 shows these measurements at two different times during the ventilation process.

Referring back to FIG. 2, based upon the measurements of the Et CO2, inspiratory O2 and expiratory O2 measurements, the system proceeds to either step 90 or step 92. In step 90, if the Et CO2 is greater than 60 mmHg or the difference between the inspiratory and expiratory O2 measurements are greater than 10%, the method proceeds to step 94. In step 94, the method generates a message to the operator to recommend an increase in the minute ventilation.

Figure 10:
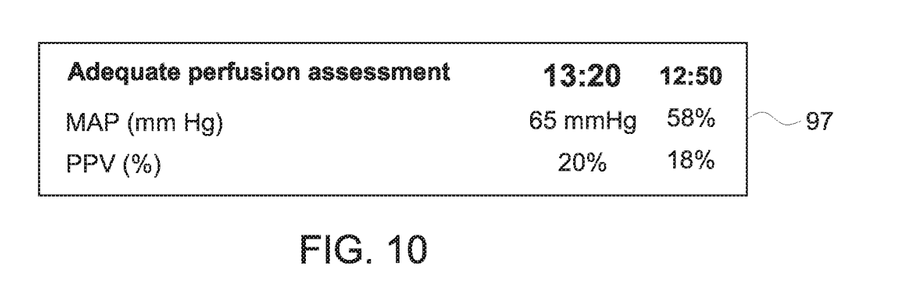
FIG. 10 is a display window showing the results of a profusion assessment.

If in step 88, which is the step that begins the Adequate Ventilation Assessment, the Et O2 and the inspired O2 are normal and the Et CO2 is less than 60 mmHg, the method moves to step 96. Step 96 begins the Adequate Perfusion Assessment process step 60 shown in FIG. 5. During this step, the system performs a process check to determine whether there is adequate blood perfusion to the patient lungs. To make this determination, the method checks the CO, blood pressure, peripheral temperature and pulse pressure variations (PPV), which are obtained from the patient monitor. The step of checking the pulse pressure variation (PPV) can be done utilizing one of many different published formulas. High PPV is a contra-indication to the lung recruitment maneuver. The measurements made at step 96 are shown to the operator, as shown by window 97 in FIG. 10. In FIG. 10, the MAP and PPV % are shown for both the current time and a previous time in the ventilation procedure.

Figure 11:
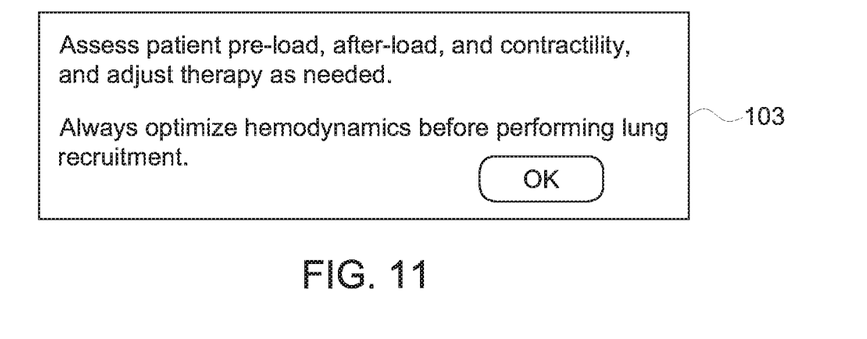
FIG. 11 is a popup window to the operator as part of the method of FIG. 2.

Based upon the measurements made in step 96, the method proceeds to either step 98 or step 100. If the patient meets the parameters shown in step 100, the method proceeds to step 102 in which it is recommended for the operator to check pre-load, after-load and contractility and to adjust the therapy as needed. This popup window is shown graphically by the popup window 103 in FIG. 11. The operator is reminded to optimize hemodynamics before performing any lung recruitment procedure.

Figure 12:
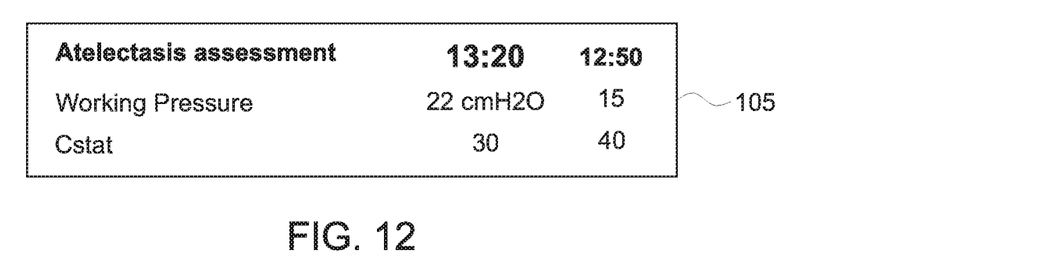
FIG. 12 is a display window showing the atelectasis assessment.

If the patient meets the parameters shown in step 98, the system moves to step 104. Step 104 is the Atelectasis Assessment step shown as one of the process steps 60 in FIG. 5. In this process step, the system and method performs an atelectasis assessment of the patient. In the atelectasis process assessment shown in step 104, the working pressure and lung compliance measurements are presented to the operator, as illustrated by window 105 in FIG. 12. Based upon these parameters, the method moves to either step 106 or step 108. In step 108, the system determines whether the lung compliance is within the normal range. This normal range can be based upon the patient length or IBW. The patient's lung compliance baseline may further vary per age and procedure type. One proposed method of determining whether the lung compliance is within a normal range for the patient, as shown in step 109, is whether the static compliance is 30% or more below the patient baseline or utilizing a normal ratio of 1 kg patient ideal body weight corresponding to 1 ml/$H_2O$ compliance.

In addition, since step 104 checks the airway resistance of the patient, the output of step 104 can depend on the value of the airway resistance. If the airway resistance provides an indicator of airway occlusion, which indicates that a lung recruitment procedure is not the correct choice for the patient. In such a case, the method 50 of FIG. 2 would not proceed to suggest a lung recruitment procedure. Instead, high airway resistance may indicate patient bronchoconstriction, which would require a bronchodilator medication.

High airway resistance could also indicate an endotracheal tube occlusion, which would require either suction or repositioning of the endotracheal tube. Either or both of these suggestions could be presented to the operator following the review of the airway resistance in step 104.

In yet another contemplated embodiment, the method 50 can check pre-load, after-load and contractility and provide a suggestion to the operator of any need to adjust therapy before or in an alternative to the lung recruitment. The system and method could also automatically adjust the therapy parameters to optimize hemodynamics without the need for the operator/clinician intervention.

Figure 13:
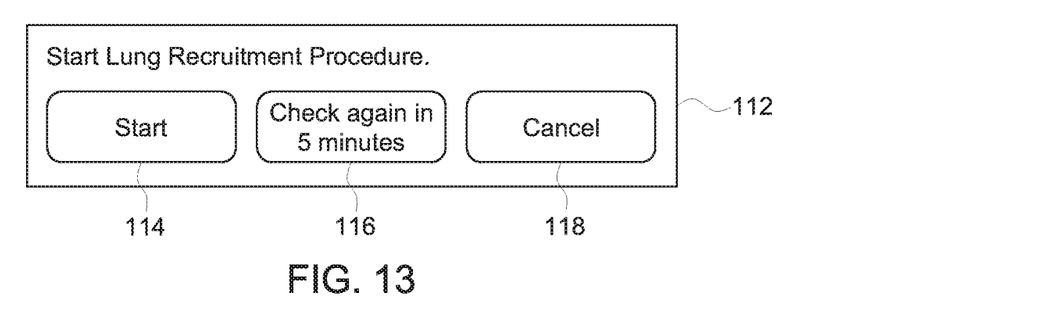
FIG. 13 is a popup prompt indicating whether lung recruitment should begin.

If the results of step 104 result in a determination that the lung compliance is 30% lower than the normal range or patient baseline, the system proceeds to step 110 in which the method recommends the beginning of a lung recruitment procedure. If the system determines that the lung recruitment procedure is necessary, as determined in step 110, a popup window 112 is generated to the operator, as shown in FIG. 13. The popup window 112 shown in FIG. 13 presents three separate options to the operator, which include starting the lung recruitment procedure 114, checking back again in an amount of time, such as five minutes, shown by button 116 and a cancel button 118 that allows the operator to completely ignore the suggestion to begin the lung recruitment procedure.

Figure 14:
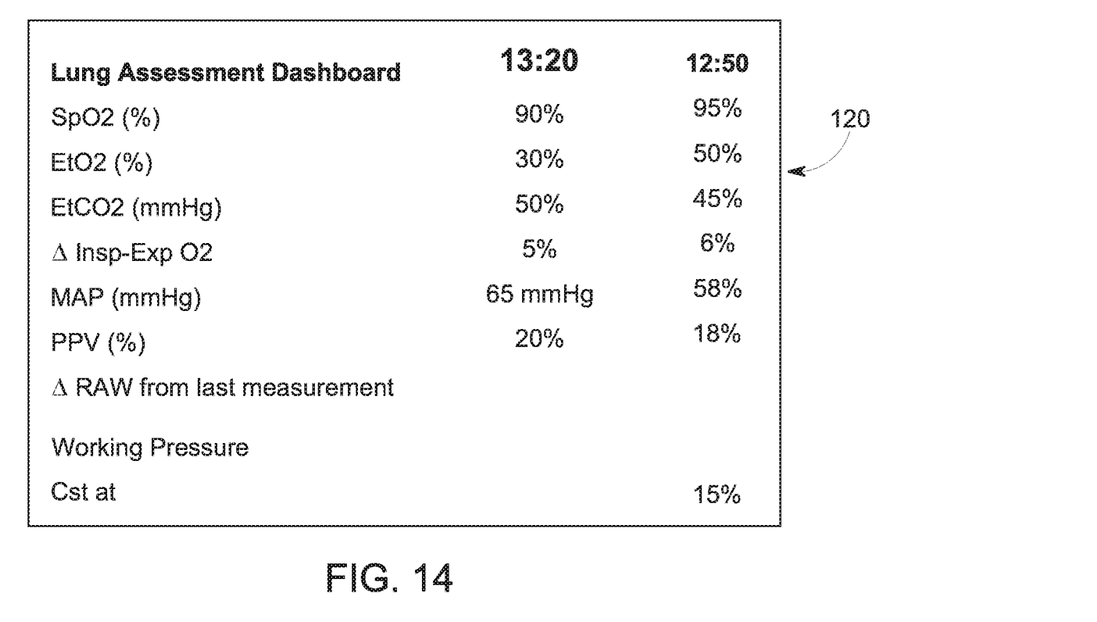
FIG. 14 is a summary of the lung assessment based upon parameters measured from the patient.

Referring now to FIG. 14, prior to beginning or initiating a lung recruitment procedure, the operator can be presented with a lung assessment dashboard, such as shown in FIG. 14. In the lung assessment dashboard 120, the operator is presented with a summary of the various parameters measured by the method of FIG. 2 such that the operator can view the various parameters in a single location to better determine whether the lung recruitment procedure should be started. The right column of the dashboard of FIG. 14 shows the previous patient measured parameters, from thirty minutes ago, along with the most recently measured parameters. Although the default is to show the most recent parameters and the previously obtained measurements, the operator can select various different time periods during the ventilation cycle to view the various important lung parameters.

Figure 15:
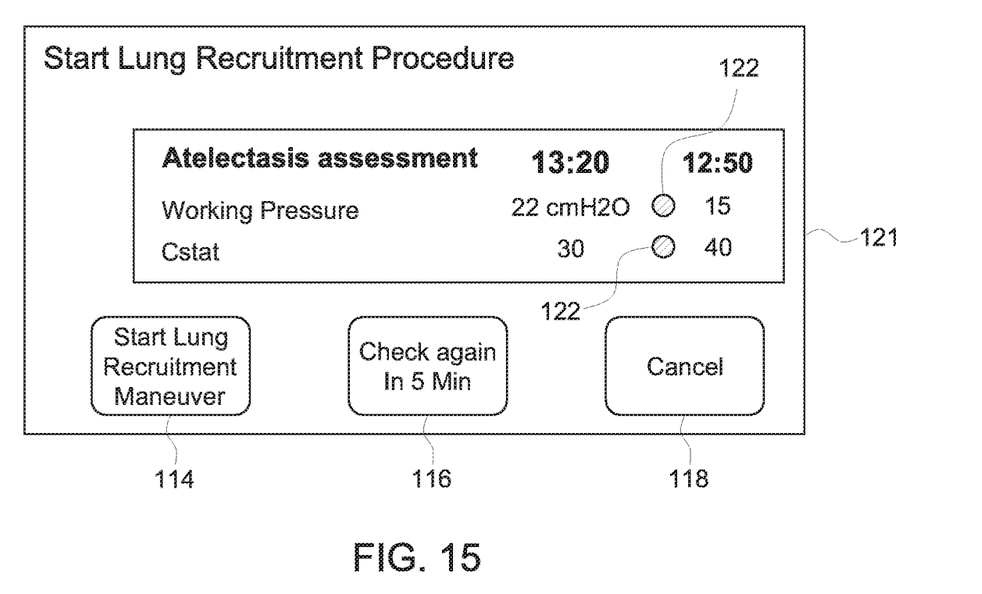
FIG. 15 is a popup window prompting the operator to begin a lung recruitment procedure.

In accordance with the present disclosure, the lung recruitment procedure can be triggered by the operator in at least two different ways. The first of the two ways is as a result of the method shown in FIG. 2, which is presented to the operator with the screen popup window 113 shown in FIG. 15. The screen popup shown in FIG. 15 generally combines FIGS. 12 and 13 to present information to the operator. Colored indicators 122 can be used to indicate that the two parameters shown fall outside of normal ranges, which was the reason for indicating the desire for the starting of a lung recruitment procedure.

Figure 16:
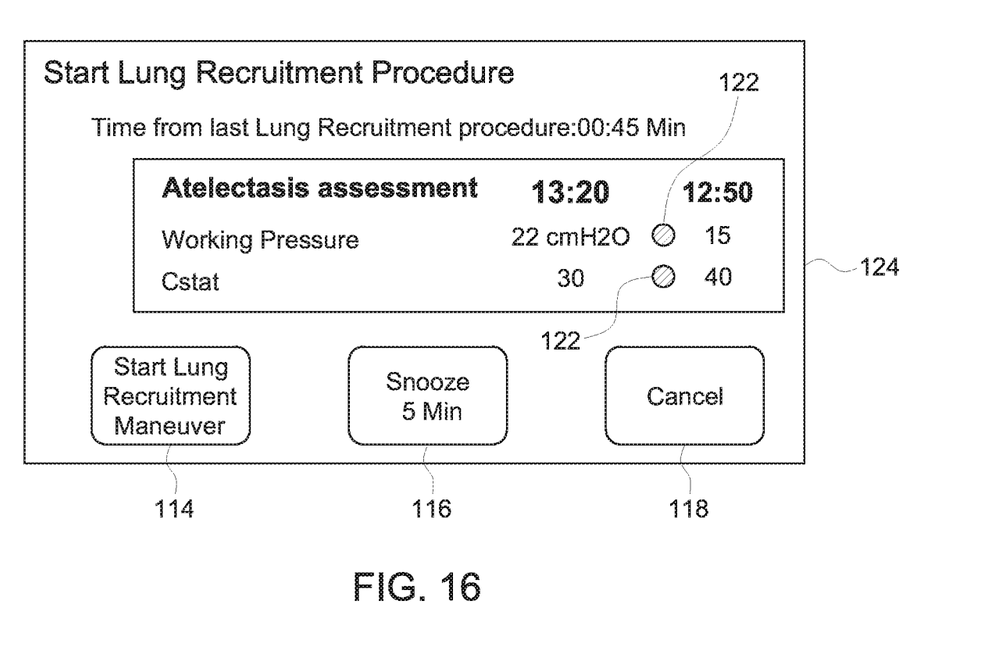
FIG. 16 is a popup window indicating whether a lung recruitment procedure should begin after the expiration of a time period.

If the operator selected to begin the procedure at a set time after the last procedure, the method generates a popup reminder 124 after the expiration of the time period from the last lung recruitment as shown in FIG. 16. As was discussed with respect to FIG. 3, the user can select when the lung recruitment procedure should begin, including within a selected period of time from the last lung recruitment procedure. In the popup reminder message shown in FIG. 16, the operator is again presented with colored indicators 122 relating to whether the measured parameters are outside of normal operating ranges. The popup window 124 presents the operator with the same buttons 114, 116 and 118 that allow the operator to determine whether the lung recruitment maneuver should start, should be delayed or should be cancelled. In this manner, the operator is able to decide whether or not to start the recruitment procedure upon an automated prompt generated by the system and method of the present disclosure.

If the operator decides to select the button 116 indicating that the operator should be prompted again in 5 minutes, the recruitment algorithm and method shown in FIG. 2 is disabled for five minutes. After five minutes, the algorithm is run again and if the algorithm again indicates that recruitment should be carried out, the popup window shown in FIG. 15 will again be presented to the operator.

If the operator selects the cancel button 118, the procedure will be aborted. The method and algorithm of FIG. 2 will continue to run but popup windows will be disabled for the rest of the case. Passive messages may be shown on the main display screen but no action will be required by the operator.

In yet another alternate embodiment, the processor that controls the operation of the ventilator could be programmed to automatically begin a lung recruitment procedure as a result of the method 50 shown in FIG. 2. In such an embodiment, instead of presenting the operator with the popup window 121 of FIG. 15 or the popup window 124 of FIG. 16, the processor would automatically begin the lung recruitment procedure. The processor may be programmed to provide a visual indicator to the operator that a lung recruitment procedure was about to begin which would allow the operator to terminate the lung recruitment procedure if desired. However, the processor would automatically begin the procedure without the need for the operator to actuate the button 114 shown in both FIGS. 15 and 16.

Figure 17:
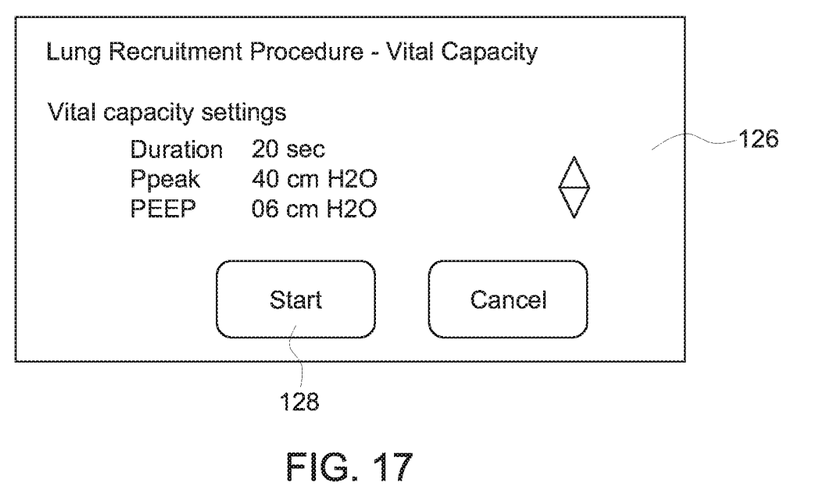
FIG. 17 is a popup window allowing the operator to modify lung recruitment procedure parameters.

During the actual lung recruitment procedure, the system and method opens a window 126 on the display which provides the current vital capacity lung recruitment settings as shown in FIG. 17. The display shown in FIG. 17 allows the operator to optionally adjust the vital capacity settings and begin the recruitment procedure by clicking on the start button 128.

Figure 18:
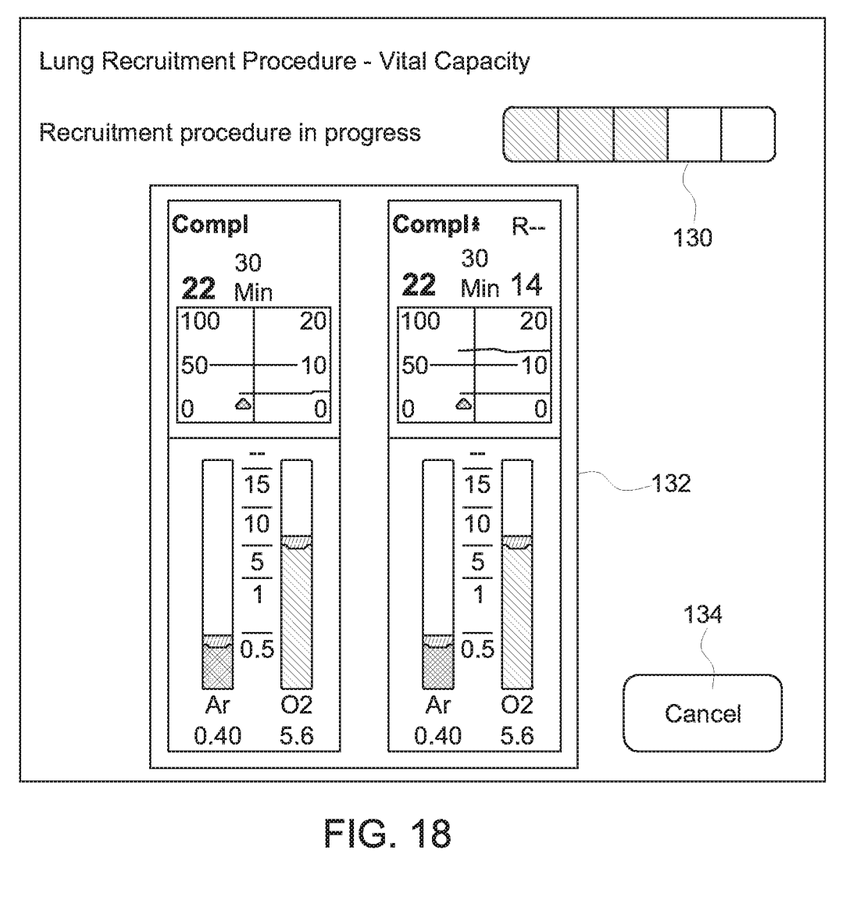
FIG. 18 is a popup window showing the lung recruitment progress and various parameters germane to the lung recruitment.

Once the actual recruitment procedure begins, another window, such as shown in FIG. 18, opens which presents a time count and graphical progress bar 130 to the operator. Live monitored patient data can be presented on the main screen, including the portions 132 shown in FIG. 18. The clinician can abort the recruitment procedure by clicking on a cancel button 134.

Once the recruitment procedure has been completed, a summary window 136 is presented to the operator. In the summary window 136 shown in FIG. 19, an atelectasis index score is presented to the user both before and after the recruitment procedure. A separate indicator 138 can be used to visually indicate whether the index is acceptable. As an example, before the recruitment procedure, the indicator 138 is red indicating the index is outside of a normal range while after the recruitment procedure, the indicator is green indicating the index is within a normal range. The colored indicators 138 provide quick and easy indicators to the operator as to whether the recruitment procedure was successful. The user is prompted by button 140 to confirm that the recruitment procedure has been completed and is acceptable.

Figure 19:
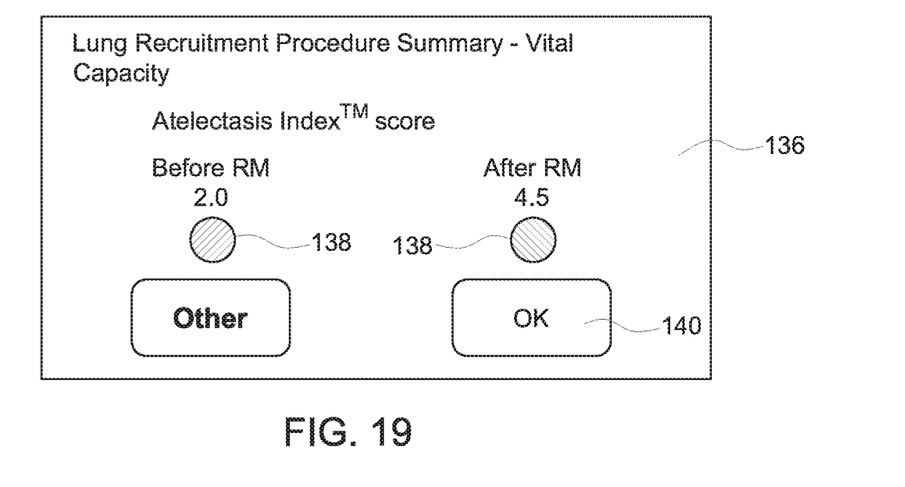
FIG. 19 is a popup window indicating the results of an atelectasis index before and after a lung recruitment procedure.

In another alternate embodiment, the method and system can present the measured patient parameters after completion of the lung recruitment procedure and the clinician can determine the success level of the procedure. This embodiment would provide direct clinician analysis, which can be used as data to aid in recruitment and ventilation analytics. Such embodiment could be used alone or in combination with the colored indicators 138.

At the end of each recruitment procedure, a recruitment summary will be provided. In addition, the data generated and stored during the recruitment procedure can be gathered and provided to the facility either through an onboard storage system, communication to remote storage facility or by providing data to cloud storage. The various different lung recruitment procedures can then be analyzed to create post usage analytics that will help optimize the lung recruitment procedure and may be used for automatically adjusting the default parameters utilized to determine when a lung recruitment procedure is needed. The recruitment process summary can also be used to evaluate the operator performance in determining whether the lung recruitment procedure was needed. As a result of the aggregation of a large number of procedures, staff compliance, education and outcome reporting can be another benefit of the method and system of the present disclosure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed:

1. A method of determining when to carry out a lung recruitment procedure on a patient receiving respiratory support from a mechanical ventilator, the method comprising:
   obtaining a plurality of patient parameters from the patient at a first time period during the respiratory support;
   setting a plurality of default parameters and storing the default parameters in a processor;
   comparing the obtained patient parameters from the first time period to the default parameters in the processor;
   recommending at least one action based on the comparison between the obtained patient parameters and the default parameters;
   obtaining the plurality of patient parameters at a second time period that is after completion of the at least one action;
   comparing the obtained patient parameters from the second time period to the default parameters in the processor after the completion of the at least one action; and
   recommending the lung recruitment procedure after the completion of the at least one action based on comparison after the completion of the at least one action.

2. The method of claim 1 further comprising the steps of:
   presenting a plurality of lung recruitment procedure types to an operator; and
   receiving a selection of one of the lung recruitment procedure types from the operator.

3. The method of claim 2 further comprising the steps of:
   presenting the default parameters for the selected lung recruitment procedure type to the operator; and
   allowing the operator to adjust the default parameters.

4. The method of claim 1 wherein the step of recommending the lung recruitment procedure includes requesting an initiation of the lung recruitment procedure from an operator.

5. The method of claim 1 wherein one of the plurality of patient parameters is SpO2 concentration, wherein the recommended action is checking the position of an SpO2 sensor when the SpO2 concentration is below a default SpO2 concentration.

6. The method of claim 1 wherein one of the plurality of patient parameters is Et O2 concentration, wherein the recommended action is increasing FiO2 when the Et O2 concentration is below a default Et O2 concentration.

7. The method of claim 1 wherein the plurality of patient parameters include Et CO2, inspiratory O2 and expiratory O2, wherein the recommended action is to increase minute ventilation when the Et CO2 is above a default Et CO2 concentration or the inspiratory O2 and expiratory O2 difference is greater than a default difference percentage.

8. The method of claim 1 wherein the plurality of patient parameters include lung compliance, wherein the recommended action is lung recruitment when the lung compliance is below a default percentage from a normal range.

9. The method of claim 1 wherein the step of recommending lung recruitment includes presenting choices of delaying lung recruitment or starting lung recruitment.

10. A method of determining when an operator should carry out a lung recruitment procedure on a patient receiving respiratory support from a mechanical ventilator, the method comprising:
    setting a plurality of default parameters and storing the default parameters in a processor;
    obtaining SpO2 concentration from the patient;
    recommending to the operator checking the position of an SpO2 sensor when the SpO2 concentration is below a default SpO2 concentration;
    obtaining Et O2 concentration from the patient following the checking the position of the SpO2 sensor;
    recommending to the operator increasing FiO2 when the Et O2 concentration is above a default Et O2 concentration;
    obtaining Et CO2, inspiratory O2 and expiratory O2 from the patient following the increase of the FiO2;
    recommending to the operator increasing minute ventilation when the Et CO2 is above a default Et CO2 concentration or the inspiratory O2 and expiratory O2 difference is greater than a default difference percentage
    obtaining lung compliance from the patient following the increase in the minute ventilation;
    recommending lung recruitment when the lung compliance is below a default percentage from a normal range and following the completion of the recommended action by the operator.

11. The method of claim 10 further comprising the steps of:
    presenting a plurality of lung recruitment procedure types to the operator; and
    receiving a selection of one of the lung recruitment procedure types from the operator.

12. The method of claim 11 further comprising the steps of:
    presenting the default parameters for the selected lung recruitment procedure type to the operator; and
    allowing the operator to adjust the default parameters.

13. The method of claim 10 wherein the step of recommending the lung recruitment procedure includes requesting an initiation of the lung recruitment procedure from the operator.

14. A method of determining when to carry out a lung recruitment procedure on a patient receiving respiratory support from a mechanical ventilator, the method comprising:
- obtaining a plurality of parameters from the patient during the respiratory support;
- setting a plurality of default parameters and storing the default parameters;
- carrying out a plurality of sequential process steps based on differences between the obtained parameters from the patient and the default parameters; and
- recommending the lung recruitment procedure only after the completion of the plurality of process steps.

15. The method of claim 14 wherein the plurality of process steps include at least an oxygen supply assessment that compares SpO2 and Et 02 values from the patient to default parameters.

16. The method of claim 15 wherein the plurality of process steps includes a ventilation assessment that compares Et CO2, inspired O2 and expired O2 to default parameters.

17. The method of claim 16 wherein the plurality of process steps includes a perfusion assessment that compares mean arterial pressure, peripheral temperature and PPV to default parameters.

18. The method of claim 17 wherein the plurality of process steps includes an atelectasis assessment that compares working pressure and lung compliance to default parameters.

19. The method of claim 14 further comprising the steps of:
- presenting a plurality of lung recruitment procedure types to the operator; and
- receiving a selection of one of the lung recruitment procedure types from the operator.

20. The method of claim 14 further comprising the steps of:
- presenting the default parameters for the selected lung recruitment procedure type to the operator; and
- allowing the operator to adjust the default parameters.

\* \* \* \* \*